(12) United States Patent
Kojima et al.

(10) Patent No.: US 6,936,152 B2
(45) Date of Patent: Aug. 30, 2005

(54) CAPILLARY ARRAY ELECTROPHORESIS APPARATUS AND METHOD OF SEPARATING AND ANALYZING SPECIMEN

(75) Inventors: Masaya Kojima, Mito (JP); Muneo Maeshima, Mito (JP); Yoshiyuki Okishima, Minori (JP); Tomohiro Shoji, Hitachinaka (JP); Wataru Matsuo, Mito (JP)

(73) Assignee: Hitachi, Ltd., Tokyo (JP)

( * ) Notice: Subject to any disclaimer, the term of this patent is extended or adjusted under 35 U.S.C. 154(b) by 818 days.

(21) Appl. No.: 09/852,029

(22) Filed: May 10, 2001

(65) Prior Publication Data

US 2002/0003091 A1 Jan. 10, 2002

(30) Foreign Application Priority Data

May 15, 2000 (JP) ......................... 2000-147495

(51) Int. Cl.[7] .......................... C25B 13/02; G01N 27/27
(52) U.S. Cl. ..................... 204/601; 204/602; 204/603
(58) Field of Search ............................... 204/601, 602, 204/603

(56) References Cited

U.S. PATENT DOCUMENTS

| 5,085,757 | A | * | 2/1992 | Karger et al. ............... 204/603 |
| 5,274,240 | A | * | 12/1993 | Mathies et al. .......... 250/458.1 |
| 5,366,608 | A | | 11/1994 | Kambara |
| 5,439,578 | A | | 8/1995 | Dovichi et al. |
| 5,516,409 | A | | 5/1996 | Kambara |
| 5,529,679 | A | | 6/1996 | Takahashi et al. |
| 5,582,705 | A | | 12/1996 | Yeung et al. |
| 5,730,850 | A | | 3/1998 | Kambara et al. |
| 5,790,727 | A | | 8/1998 | Dhadwal et al. |

* cited by examiner

*Primary Examiner*—Ling-Sui Choi
(74) *Attorney, Agent, or Firm*—Dickstein Shapiro Morin & Oshinsky LLP

(57) ABSTRACT

At a wall constituting a space for a thermostatic oven in an electrophoresis apparatus, a capillary array attachment portion is formed which permits attachment of a plurality of capillary arrays having different length. Thereby, a selected capillary array constituted by collecting a plurality of capillaries can be easily attached to the electrophoresis apparatus depending on measurement purpose.

28 Claims, 14 Drawing Sheets

CAPILLARY ARRAY ELECTROPHORESIS APPARATUS AND METHOD OF SEPARATING AND ANALYZING SPECIMEN

BACKGROUND OF THE INVENTION

1. Field of the Invention

The present invention relates to a capillary array electrophoresis apparatus and a method of separating and analyzing specimen which can be used for separating and analyzing specimen such as DNA and protein.

2. Conventional Art

An application technology in which an array is constituted by combining a plurality of capillaries, an electrophoresis medium and a sample to be separated or analyzed are supplied to the respective capillaries and moved therethrough to thereby separate and analyze the object sample is well known, wherein a sample such as DNA and protein marked by a fluorescent material is supplied to the capillaries. Such application technology is, for example, disclosed in U.S. Pat. Nos. 5,366,608, 5,529,679, 5,516,409, 5,730,850, 5,790,727, 5,582,705, 5,439,578 and 5,274,240. In view of a through-put of the separation and analysis, it is much more advantageous to use electrophoresis with multi capillaries rather than electrophoresis with a flat plate gel.

A capillary array electrophoresis apparatus is basically constituted by such as a capillary array, an excitation light system including a laser beam source, a light receiving optical system which detects fluorescence and a voltage application unit which causes electrophoresis. In such capillary array electrophoresis apparatus, the capillary array is constituted by aligning a plurality of capillaries in a plane shape, and a laser beam is irradiated to the capillaries which are filled with a sample (fluorescent sample) marked by a fluorescent material in parallel direction with the capillary aligning direction, then, through the lens action of the capillaries the laser beam is condensed and the laser beam is irradiated to the fluorescent sample in all of the capillaries when the laser beam is irradiated, the fluorescent sample emits fluorescent. Through detection by the light receiving optical system of the fluorescent emitted from the fluorescent sample in a direction substantially perpendicular to the laser beam irradiation direction, the measurement of the sample is performed.

Since time required for electrophoresis, separation and resolution differ depending on molecular weight and molecular structure of the object sample, it is necessary to change the length of electrophoresis passage depending on the object sample. Therefore, it becomes necessary to selectively dispose several kinds of capillary arrays in a space of a thermostatic oven.

SUMMARY OF THE INVENTION

An object of the present invention is to provide a capillary array electrophoresis apparatus which permits easy handling, when exchanging a consumable capillary array therein.

The present invention provides a capillary array electrophoresis apparatus comprising, a thermostatic oven which permits temperature adjustment and includes a space which can accommodate a plurality of capillary arrays of different length exchangeably, a capillary array which is selected depending on an object sample and is disposed in the space; means for supplying the object sample into capillaries in the capillary array from one end of the capillary array; means for supplying an electrophoresis medium into the capillaries from the other end of the capillary array; means for irradiating light beam to the object sample existing within the capillaries in the capillary array at the out side of the thermostatic oven and for causing emission of fluorescence therefrom; and means for detecting the fluorescence. Thereby, a capillary array can be selected depending on an object sample to be separated and analyzed and a capillary array can be easily attached within a space of a thermostatic oven.

Further, the present invention provides a capillary array electrophoresis apparatus in which a plurality of fans each having different air suction and air discharge directions are disposed substantially most separate positions in the space of the thermostatic oven to agitate the air therein. With such arrangement of the plurality of fans the air within the space in the thermostatic oven is desirably agitated without vibrating the capillary array.

Still further, the present invention is to provide a capillary array electrophoresis apparatus comprising a first syringe having a predetermined volume, a second syringe having a smaller volume than that of the first syringe and a pump device which injects under pressure an electrophoresis medium to the first syringe and further injects under pressure the electrophoresis medium of a predetermined amount from the first syringe to the second syringe through a check value, wherein the volume of the second syringe is determined in view of the amount of the electrophoresis medium consumed substantially in an one time separation and analysis. Thereby, with the provision of such electrophoresis medium supply system a series of operation from recharging of the medium, supplying of the sample and to separation and analysis of the sample can be automated.

Still further, the present invention is to provide a capillary array electrophoresis apparatus in which major elements in the fluorescent detection means are substantially arranged on one plane face and the respective capillaries at the irradiation and detection portion in the capillary array are aligned so as to cross to the one plane face. Through such arrangement of the capillary array and the optical system, a compact separation and analysis system can be obtained.

Still further, the present invention is to provide a capillary array electrophoresis apparatus in which the sample is supplied to the one end of the capillary array from the bottom portion in the space of the thermostatic oven, the other end of the capillary array containing the sample subjected to electrophoresis is projected from the side portion of the space and the laser beam is irradiated onto the projected capillary array, thereby, fluorescence is outputted. With this arrangement of the capillary array a compact electrophoresis apparatus can be obtained.

Still further, the present invention is to provide a capillary array electrophoresis apparatus in which an array plane face constituting the detection portion of the capillary array is arranged to be substantially in parallel with the laser beam. With such arrangement of the capillary array and the optical system a compact electrophoresis apparatus can be obtained.

Still further, the present invention is to provide a method of separating and analyzing sample in which a capillary array is disposed in a space of a thermostatic oven which permits temperature adjustment and includes the space which can accommodate a plurality of capillary arrays of different length exchangeably, an object sample is supplied into capillaries in the capillary array from one end of the capillary array; an electrophoresis medium is supplied into the capillaries from the other end of the capillary array so as to fill the capillaries; laser beam is irradiated to the object sample existing within the capillaries in the capillary array at a range of the capillary array projecting from the space of the thermostatic oven; and fluorescence emitted by the laser beam irradiation is detected.

DETAILED DESCRIPTION OF THE PREFERRED EMBODIMENTS

Hereinbelow, embodiments of the present invention will be explained in detail with reference to the drawings.

Figure 1:
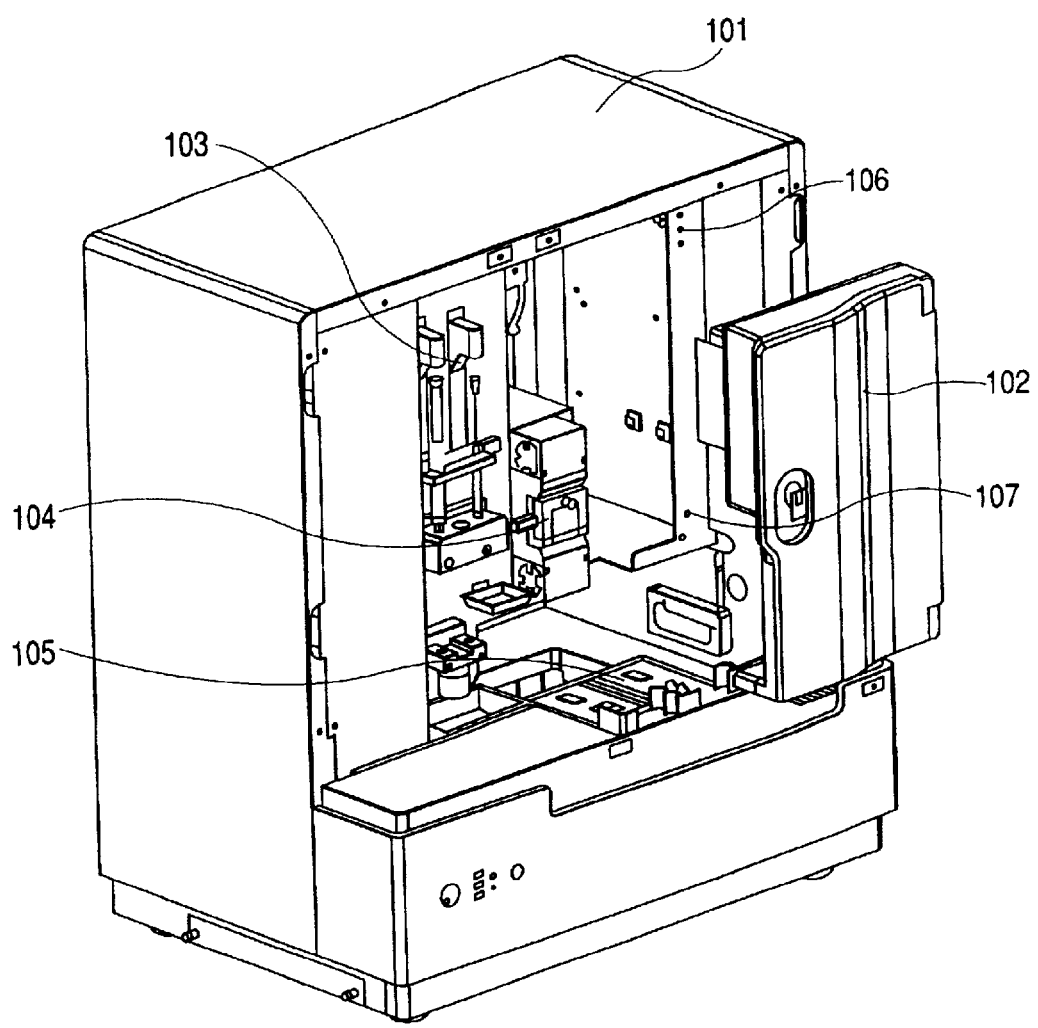
FIG. 1 is an outlook perspective view of a capillary array electrophoresis apparatus according to the present invention.

FIG. 1 shows a state in which a thermostatic oven 102 is detached from a DNA sequencer frame 101. A DNA sequencer includes, other than the thermostatic oven 102, a gel pump unit 103 which recharges and exchanges gel polymer working as a separation medium into capillaries and a irradiation and detection portion 104 which irradiates such as laser beam onto the capillary array and detects fluorescence therefrom, and further includes an auto sampler 105 for a continuous measurement.

When attaching and detaching the thermostatic oven 102 to the frame 101 for assembling and maintenance thereof, it is desirable that a correct positional relationship is always kept with the frame 101. The capillary array is to be attached to the thermostatic oven 102, thus if the positional relationship of the thermostatic oven 102 with respect to the frame 101 is not kept, the positional relationship with the auto sampler 105 is lost which requires a mechanical correction in a high possibility. In the present invention, guide pins 106 and 107 are provided for the frame 101 so as to maintain a correct positional relationship with the thermostatic oven 102.

Figure 2:
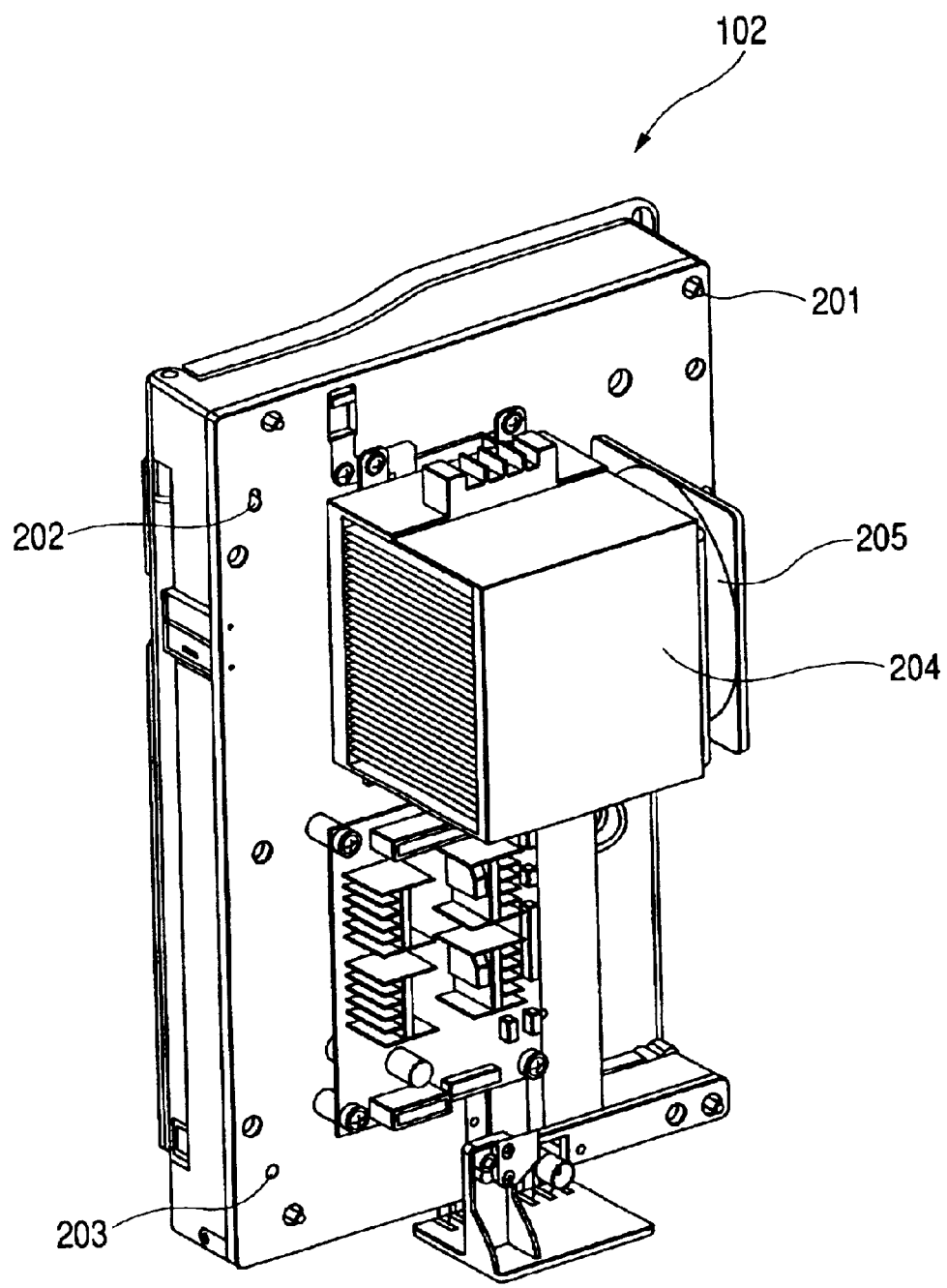
FIG. 2 is a perspective view of a thermostatic oven in FIG. 1.

FIG. 2 is a view of the thermostatic oven 102 seen from the back face thereof. On a reference plate of the back face guide holes 202 and 203 are formed at the positions corresponding to the guide pins 107 and 106 as shown in FIG. 1. When a positional accuracy for fitting between these pins and holes is determined smaller than the tolerance which is required when attaching and detaching the thermostatic oven 102, a correct positional relationship can be maintained. The required positional accuracy is determined either by a positional accuracy requiring no correction or by a positional accuracy which permits correction by a software. Herein, when a positional relationship is kept at the time of attachment, the thermostatic oven 102 is secured to the frame 101 by stationary screws 201. It is preferable to use a plurality of stationary screws 201.

Further, the thermostatic oven 102 in the present embodiment uses a Peltier element as a heat source for heating and cooling which permits, other than a set temperature more than 50° C. which is used in a normal DNA sequencer, to set a temperature below a room temperature. At the back face of the thermostatic oven a heating and cooling device is provided, wherein a heat radiation fin for a Peltier unit 204 is provided and with a Peltier heat radiation fan 205 a heat exchange efficiency is enhanced.

Figure 3:
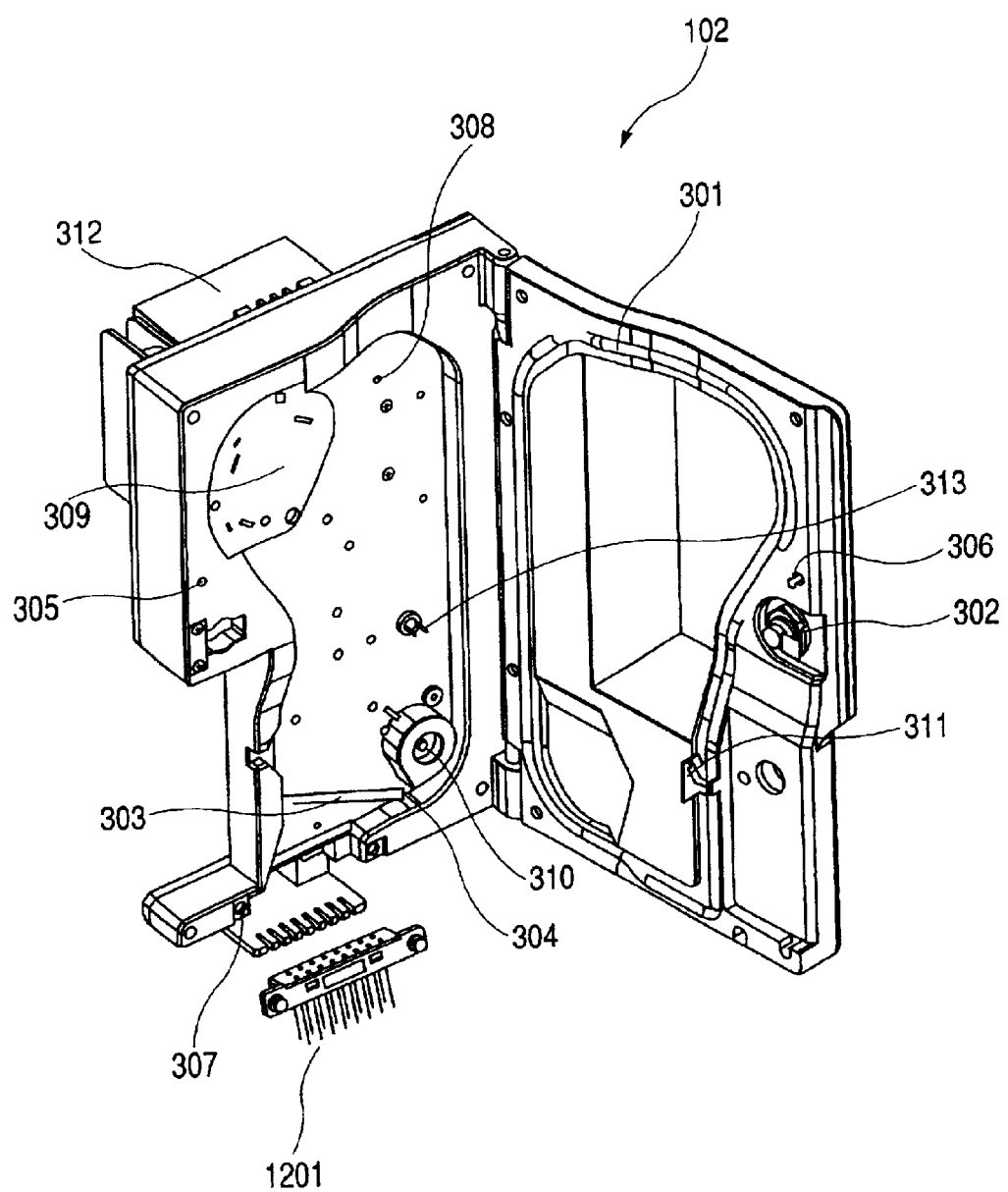
FIG. 3 is a perspective view of the thermostatic oven in FIG. 2, when the door thereof is opened.

FIG. 3 shows a view when the door of the thermostatic oven 102 is opened. A packing 301 is disposed around the door, when the door is locked by a lock 302 while pressing the packing 301, a close contact between the thermostatic oven 102 and the door is ensured, thereby, an air flow therebetween is prevented. Thus, a temperature distribution and variation within the thermostatic oven 102 are suppressed small.

At an attachment portion 307 of the capillary array it is necessary to maintain a relative positional relationship between the attached capillary array and the auto sampler, therefore, an elastic packing can not be used there, thus an air flow therethrough can not be kept zero. When the apparatus is used under an environment of high temperature and high humidity and the control temperature in the thermostatic oven 102 is lower than the room temperature, it is possible that such as steam contained in the originally existing air inside the thermostatic oven 102 and steam newly entered into the thermostatic oven 102 through air flow therebetween condense into dews. When water drops produced due to the dew condensation flow and reach to a bottom portion (around the array attachment portion) of the thermostatic oven 102, it is possible that an arc discharge is caused around the array attachment portion which is near an electrode being applied of a high voltage. For this reason, a dew acceptor 303 having a structure like a rain gutter is provided inside the thermostatic oven 102. The water drops reached to the dew acceptor 303 are guided therealong to a drain hole 304 provided in the thermostatic oven 102 and is discharged outside the thermostatic oven 102 through a drain (not shown). Thereby, a possible damage of the thermostatic oven 102 by the arc discharge is prevented.

Further, the thermostatic oven 102 is provided with an interlock switch 305, and a pin 306 for the interlock switch 305 is attached on the door at the corresponding position thereto. When the door is closed the interlock switch 305 is put into a condition of being pushed, thus, the thermostatic oven 102 functions. When the door is opened, a worker can touch the irradiation and detection portion, thus, the laser beam is automatically turned off so as to ensure safety. Further, since the worker can touch to the vicinity of the heat source, the power source for Peltier elements is also automatically interrupted so as to ensure safety which is also effective to protect the Peltier elements. When the door is opened during high temperature control of the Peltier elements, the temperature in the thermostatic oven 102 suddenly drops, accordingly, the control performs a heating operation so that the temperature again restores to the set temperature. Therefore, if the door is kept opened, the control unit continues to issue the heating command which possibly damage the Peltier elements due to overloading. With the present embodiment, such accident can be prevented.

The Peltier unit 312 working as a heat source and including the heat radiation fins and the heat radiation fan is contacted to an aluminum (Al) plate 308 at the back face of the thermostatic oven 102. On the Al plate 308 an insulation film is closely adhered so as to prevent an arc discharge. The Al plate 308 transmits heat from the heat source inside the thermostatic oven 102 through heat conduction to thereby keep the temperature inside the thermostatic oven 102 constant. The temperature in the space determined by the heat from the Al plate 308 which is heated or cooled is stabilized through agitation and circulation of the air inside the thermostatic oven 102 by the fans 309 and 310 disposed therein. An Al plate 311 is closely adhered to a collecting portion of the capillary array directed to the detection portion from the thermostatic oven 102 and is disposed for diffusing heat generated at the time of high voltage application. The temperature in the space of the thermostatic oven 102 is monitored by an in-chamber temperature sensor 313 and a temperature control is performed based on the monitoring.

Figure 4:
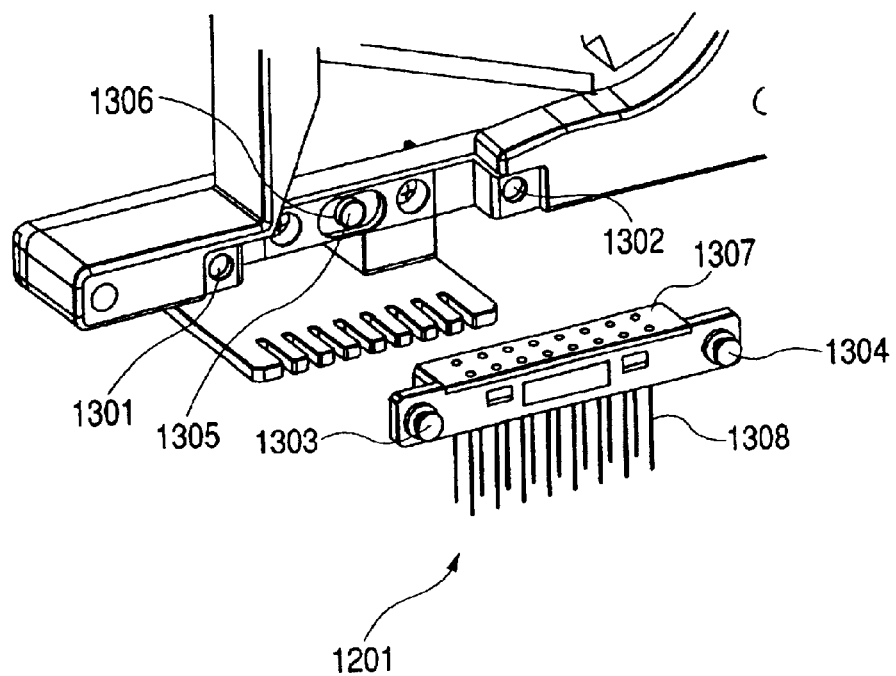
FIG. 4 is a perspective view showing a relationship between a bottom structure and a capillary array holder in the thermostatic oven as shown in FIG. 3.
Figure 5:
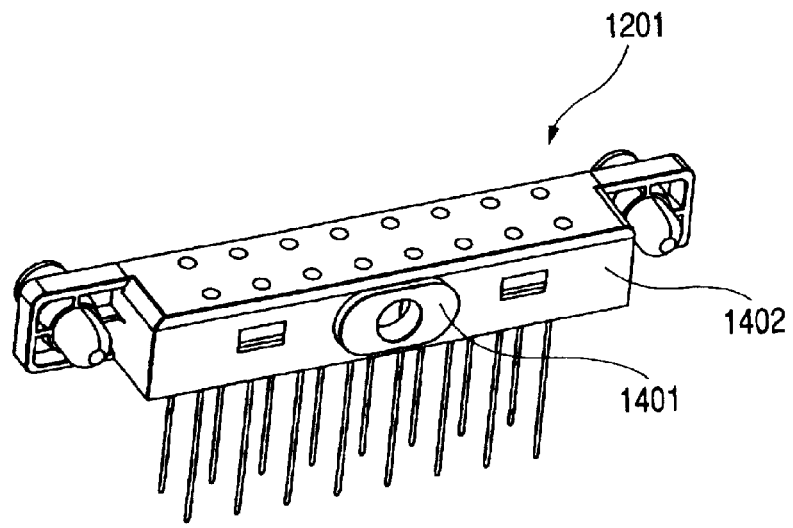
FIG. 5 is a perspective view of the capillary array holder as shown in FIG. 4, when seen from the back face thereof.

FIG. 5 shows a detail of a capillary array holder 1201. Further, FIG. 4 shows a detailed structure for attachment between the thermostatic oven 102 and the holder 1201. At the bottom portion of the thermostatic oven 102 as shown in FIG. 3, a holder 1306 for securing the capillary array holder 1201 is provided. The capillary array holder 1201 is provided with a latches 1303 and 1304 which are to be inserted into attachment holes 1301 and 1302. An electrode 1305 is provided in a recess 1306 and is connected to an electrode connection portion 1401 as shown in FIG. 5. One ends of the capillaries of the capillary array are respectively inserted one by one into holes 1307 of the capillary array holder 1201 and are connected to electrodes 1308.

Figure 8:
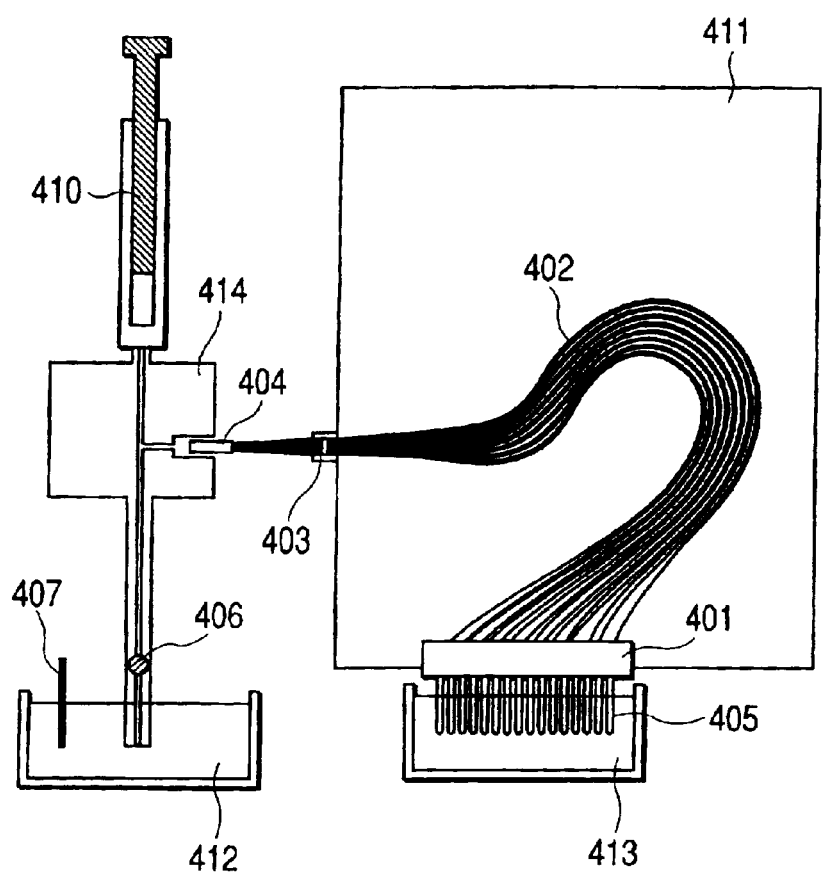
FIG. 8 is a schematic diagram showing a structure of major portions of an electrophoresis apparatus according to the present invention.
Figure 9:
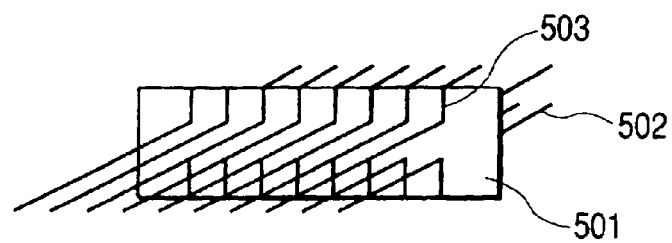
FIG. 9 is a perspective view showing a structure of a separator which aligns and holds respective capillaries in a capillary array.
Figure 12:
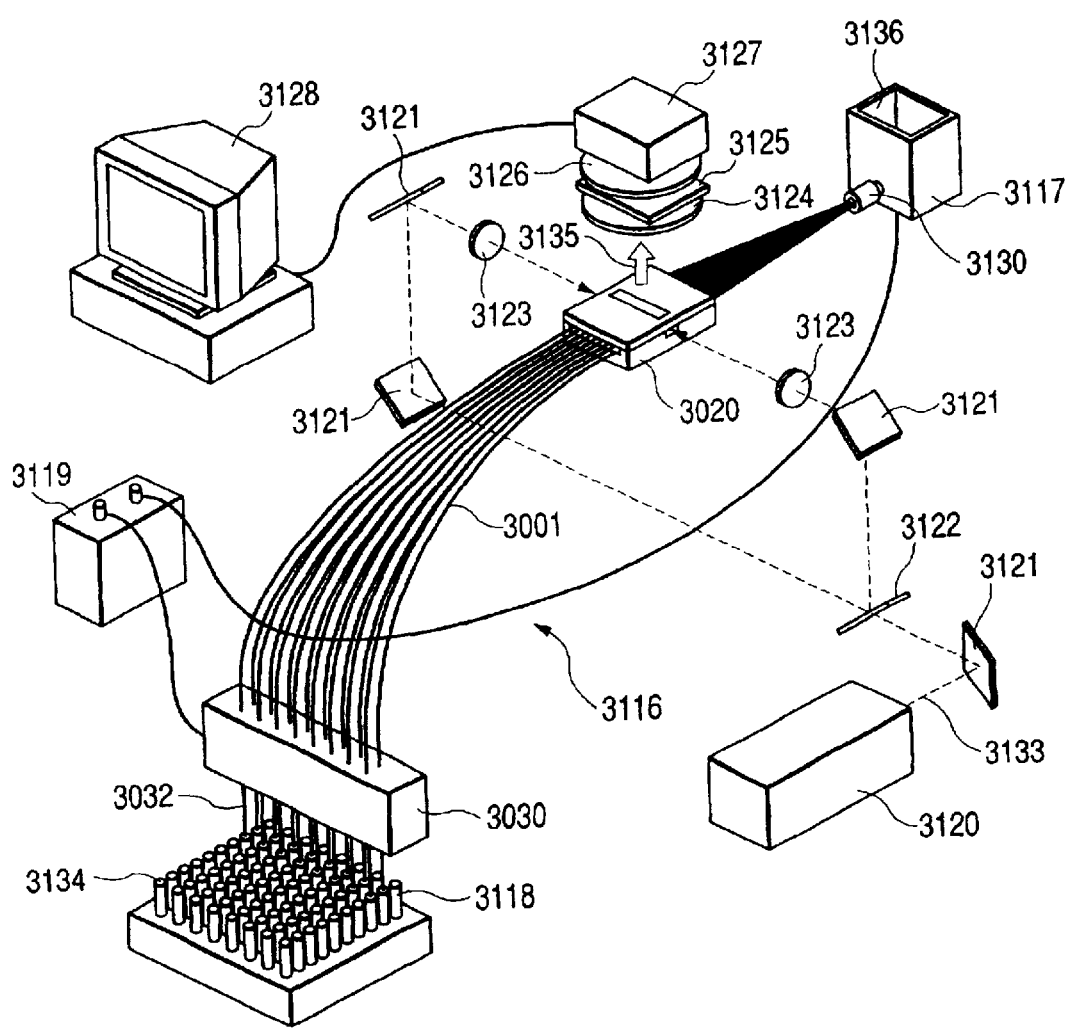
FIG. 12 is a schematic diagram for explaining laser beam irradiation and fluorescence detection in a capillary array electrophoresis apparatus according to the present invention.

A structure of the capillary array itself is shown in FIGS. 8 and 12. The capillary array will be explained with reference to FIG. 8. The capillary array is constituted by an array holder portion 401 which attaches the capillary array to the thermostatic oven, capillaries 402, a light measurement portion 403, a gel injection portion 404 and an electrode portion 405. In the present embodiment, an example of simultaneous measurement of 16 samples set at a marketed micro-tighter plate having 96 holes or 384 holes is shown. 16 pieces of capillaries 402 and electrode portions 405 are included in the capillary array. A material of the capillaries is usually fused quartz and on the surface of the capillaries except for the portion where the laser beam is irradiated and fluorescence is detected a high polymer protective coating such as polyimide is formed. In order to set the plurality of capillaries within the thermostatic oven as illustrated, in that while preventing from tangling thereof or from concentrating thereof in a bundle shape, a separator 501 as shown in FIG. 9 is used. The separator 501 is in a film or plate shape, and at both ends of the separator 501 slits 503 for holding the capillaries one by one are formed. When handling a capillary array it is preferable to preserve, manage and handle the capillary array while attaching the separator 501 as it is. The number of separators 501 can be increased depending on the length of the capillary array. For example, for a capillary array of about 36 cm one separator 501 is sufficient, but for a capillary array of about 80 cm it is preferable to attach about five separators 501.

The separator 501 is set between the array holder 401 and the light measurement portion 403 and holds the capillaries 502 so as not to tangle and concentrate. By means of the holder 401 and the separator 501, even if heat is generated from the capillaries due to the high voltage application on the capillaries during electrophoresis, the tangling and concentration of the capillaries are prevented, the heat is dissipated and a temperature increase in the separation medium during the measurement is prevented.

Figure 10A:
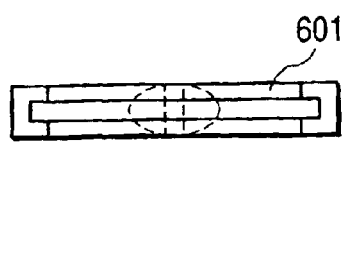
FIGS. 10A and 10B are an upper face view and a side face view showing a structure of a separator holder for holding the separator as shown in FIG. 9 on a wall of the thermostatic oven.
Figure 10B:
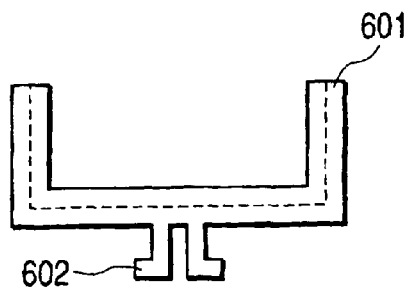

Even if ventilation is improved through the provision of the separators 501, since the capillaries are usually not a rigid body but show elasticity, it is important to always dispose the capillaries at a predetermined position in the thermostatic oven even when such as capillaries are exchanged and an operator is altered. Therefore, a separator holder 601 as shown in FIGS. 10A and 10B is used at the side of the thermostatic oven wherein FIG. 10A is a top view thereof and FIG. 10B is a side view thereof. The separator 501 is attached from the top as shown in FIG. 10A. As will be seen from FIG. 10B side view, the separator holder 601 is provided two legs 602 extending therefrom.

An attachment and detachment of the separator holder 601 to the thermostatic oven is performed in the following manner. The leg 602 is inserted into an attachment hole for the separator holder 601 which is formed on the Al plate 308 in the thermostatic oven at a position where the separator is to be set, and turns the separator holder 601 by 90°. When projecting the leg portion of the separator holder 601, the shape of the leg shows an ellipse or a long axis shape, therefore, when the leg is turned by 90°, the long axis direction of the leg becomes in parallel with the short axis of the attachment hole. Since the long axis of the leg portion is longer than the short axis of the attachment hole, the separator holder 601 is secured to the Al plate 308. When detaching the separator holder 601, the separator holder 601 is turned again by 90° so that the long axis of the leg portion becomes in parallel with the long axis of the attachment hole, thereby, the separator holder 601 can be detached from the attachment hole. Thus, the separator holder 601 can be attached and detached, easily as explained above.

When using capillary arrays having different length, number of separators are prepared depending on the respective length of the capillary arrays and are set at positions depending on the length thereof. If the separator holders can not be easily attached or detached or not totally be attached or detached, a separator holder which is not used for a certain length capillary array may interfere the capillary array now used.

Figure 11:
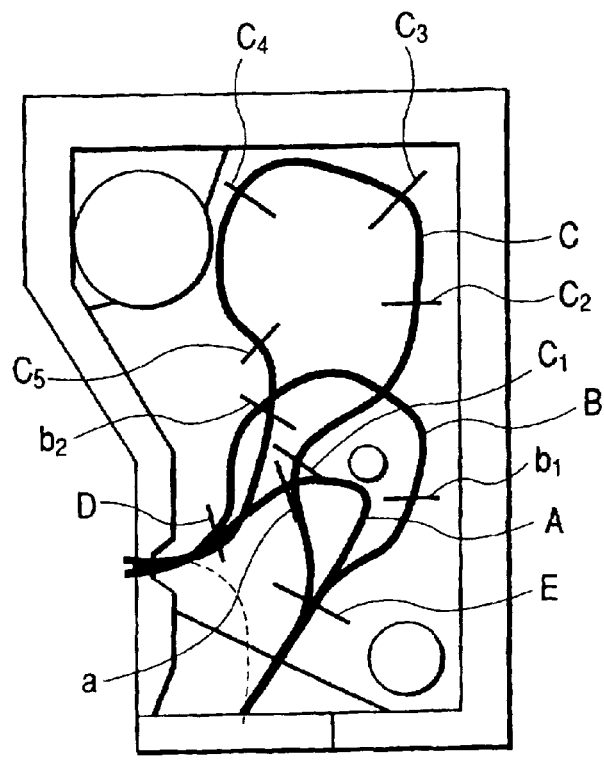
FIG. 11 is a schematic diagram showing an imaginary attachment state of a plurality of capillary arrays having different length in the thermostatic oven.

FIG. 11 is an imaginary diagram showing layouts when capillary arrays of 36 cm, 50 cm, and 80 cm, are set in the thermostatic oven and positions of separator holders used for all of capillary arrays having different length. Actually, during one time separation and analysis only one capillary array is used. Namely, when using the shortest capillary array A, the capillary array is shaped in a desirable form, disposed and held on the inner wall of the thermostatic oven by means of a common array holder E, a holder "a" for the array A and a common holder D.

When holding a comparatively long capillary array B, the capillary array is held by means of the common holder E, holders b1 and b2 and the common holder D. When holding the longest capillary array C, the capillary array is held by means of the common holder E, holders c1, c2, c3, c4 and c5 and the common holder D.

The respective separator holds are set at positions not interrupting wind blow by the fans for circulating air in view of wind blow direction in the thermostatic oven. Further, in order to minimize the number of holes formed in the Al plate 308, the holes which can be used in common are increased. In the present embodiment, the position nearest to the separate holder 601 and the position nearest to the light measurement portion are determined as the common positions. Through the common use of the separators a compact electrophoresis apparatus can be realized.

Since the separator holders are attached and detached depending on the respective length of the capillary array to be used, marks associating with the length of array which uses the concerned attachment holes are applied near the respective separator holder attachment holes on the Al plate 308 or on the insulation film closely adhered to the Al plate 308. Thereby an erroneous operation of attaching a separator holder to an erroneous attachment hole can be avoided.

Now, how the capillary array holder is attached to the thermostatic oven will be explained. FIGS. 3 through 5 show a structure and attachment position of the capillary array holder 1201. In the drawings, the illustration of the capillary portion in the capillary array is omitted. The thermostatic oven is cut out at a position where the array holder is set so that the face of the thermostatic oven which contacts the door becomes flush with the door side of the array holder when the array holder is set. Further, when the latches 1303 and 1304 attached to the capillary array holder 1201 are fitted into the respective attachment holes 1301 and 1302, the capillary array holder 1201 is secured to the thermostatic oven. This reproducibility with regard to attachment position is also important, because the same determines the relative positional relationship between the capillary array and the auto sampler. Therefore, the non-circular recess 1306 is provided on a portion of the electrode 1305 at the array holder attachment portion for the thermostatic oven. Examples of the non-circular shape are such as ellipse and long circle. FIG. 5 is a view when seen the array holder in FIG. 4 from the back face thereof. A projection 1401 is provided at a position corresponding to the recess 1306 in the thermostatic oven. When the size clearance of these recess and projection at the time of fitting is determined as in the same level as the positional accuracy required during attachment and detachment of capillary array, a reproducibility with regard to attachment and detachment position in the directions of right and left, up and down and rotation can be maintained. A positional reproducibility in backward direction is maintained through contact between the reference face 1402 of the capillary array and the opposing face of the thermostatic oven.

Further, a high voltage of more than 15 kV is applied to the electrode 1305, around the electrode there is provided a recess and an insulative rubber is laid out over the recess so as to closely contact with the projection 1401 in the capillary array holder 1201. Thereby, an air gap between the electrode 1305 and the capillary array holder 1201 is eliminated. Further, through the fitting structure between the recess and the projection a creeping distance from the high potential portion to the grounding portion is prolonged, thereby, a possible arc discharge is suppressed.

Figure 6A:
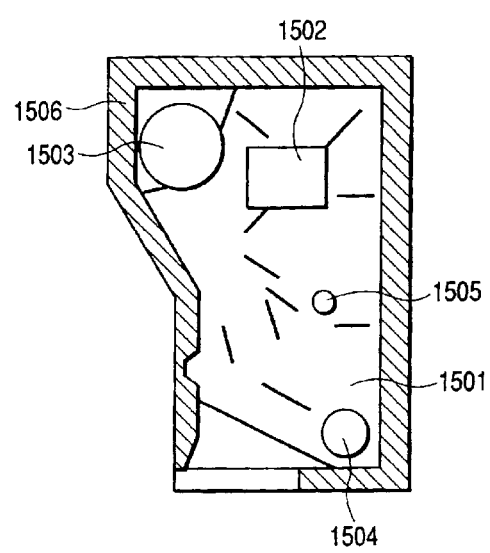
FIGS. 6A and 6B are schematic cross sectional views showing inner structure of the thermostatic oven as shown in FIG. 2.
Figure 6B:
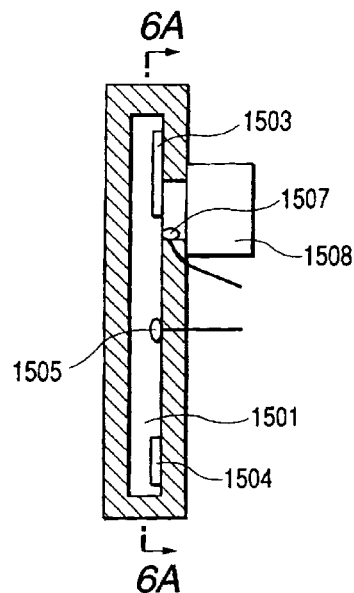

FIG. 6A is a schematic structure of the thermostatic oven shown in a plane cross sectional view and FIG. 6B in a side cross sectional view thereof. The Al plate 1501, which uniformly transfer heat from the Peltier elements working as a heat source into the thermostatic oven and stabilizes the temperature therein, is contacted to a Peltier unit 1508 from the back face of the thermostatic oven through a Peltier contact portion 1502. A reason of using a Peltier unit is that the Peltier unit can set not only a higher temperature than the room temperature but also can set a lower temperature than the room temperature. The heat transferred from the Peltier unit to the Al plate 1501 is transferred to the air in the thermostatic oven and the air is agitated and circulated by the fans 1503 and 1504 which further stabilizes the temperature of the thermostatic oven. The temperature in the thermostatic oven is monitored by a temperature sensor 1505.

The circumference of the thermostatic oven is covered by a heat insulating material 1506 and the heat flow to and from the outside of the thermostatic oven is interrupted. Further, with a Peltier temperature sensor 1507 the temperature of the Peltier unit is monitored.

Figure 7A:
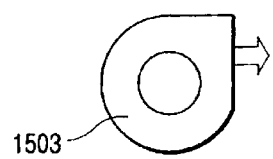
FIGS. 7A through 7D are schematic diagrams showing air flow directions of two fans disposed in the thermostatic oven.
Figure 7B:
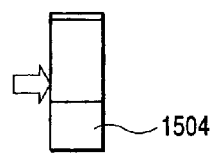
Figure 7C:
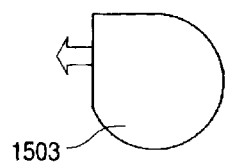
Figure 7D:
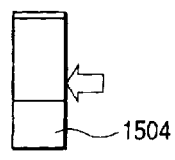

FIGS. 7A and 7B show air suction and below out directions of two flat fans used in the thermostatic oven. As illustrated in the drawings through the use of a flat fan of which air suction and blow out directions are not in parallel, the thickness of the thermostatic oven is reduced. FIGS. 7C and 7D are views when seen these fans from the back face thereof. An example when the fans are disposed as in FIGS. 7A and 7B is shown in FIGS. 6A and 6B. FIG. 6A shows the position where the fans are disposed, and is a cross sectional view seen from the arrowed direction in FIG. 6B.

When disposing the fans as illustrated in FIG. 6B, the air suction port is located at the side of the door of the thermostatic oven, in that at the position remote from the heat source. If the fans are located at the wall face in contrast to the arrangement in FIG. 6B, the air suction port locates at the opposite side of the door, in that at a position near the heat source. When the air is sucked near from the heat source, the air having temperature near the heat source other than the current temperature in the thermostatic oven can be circulated which is desirable. In an actual arrangement, the fans can be secured at the door side, however, if the fans can not be secured at the door side because of problems such as wiring, the fans can be disposed at the opposite side of the door through provision of such as a spacer and a holder at the side thereof. In the example as illustrated in FIG. 3, the fans are disposed at the opposite side of the door. As illustrated in FIG. 7A, the air blow out direction of the fan is offset from the center axis of the air suction port. Further, if it is difficult to align all of the air blow out directions in a target direction depending on the structure of fans, it is not necessary to locate all of the air suction ports of the plurality of fans at the side of the heat source, but a part of the air suction ports can be located at the side of the heat source. In the example of FIG. 3, the air suction port of the fan 309 is located at the side of the heat source, but the air suction port of the fan 310 is at the side of the door.

Further, in view of the air circulation, a fan with a large air capacity is effective because of no air holdup, however, if the capillary array is caused to vibrate because of the large air capacity which will lead deterioration in separation through the electrophoresis. Therefore, a fan having a large air capacity is disposed at a portion where no vibration affects to the capillary array and a fan having an air capacity causing no vibration is selected for a portion where vibration affects to the capillary array. In FIGS. 6A and 6B, the air capacity of the fan 1504 is selected smaller than that of the fan 1503.

Figure 17:
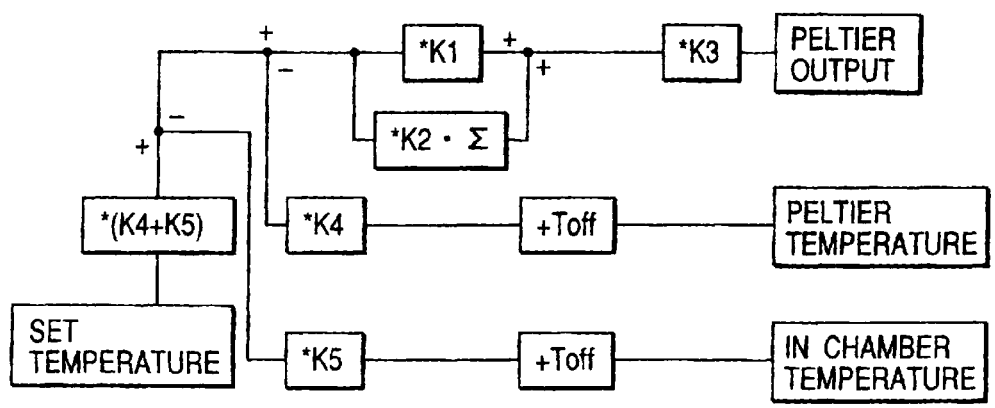
FIG. 17 is a block diagram for controlling a thermostatic oven.

In an actual temperature control, a method in which only the air temperature in the thermostatic oven is monitored and a feed back signals are applied to the output of the Peltier unit is generally used. However, in addition to the temperature sensor 1505 for the thermostatic oven, the temperature sensor 1507 for the Peltier unit can be used for the temperature control. FIG. 17 shows a block diagram for explaining an exemplary temperature control which is an example of a proportional and integration control. In the drawing K1 through K5 are control constants, and +Toff is a correction constant which is used and processed by a software when read indication values from the respective sensors include offset and usually zero. K1 is a proportional coefficient. K2·Σ is an integration term which represents that after multiplying integration constant K2 an integration is performed.

The a final resultant output of the control is the Peltier out, and response of the Peltier temperature to the Peltier output is quick and direct. On the other hand, the response of the temperature in the thermostatic oven to the Peltier output is slow and indirect. Therefore, when the Peltier temperature is used for the control, a long waviness of temperature time constant can be reduced in comparison with when only the temperature of slow response in the thermostatic oven is used for the control which is desirable for the present control.

In the present invention, all of the three functions necessary for a capillary array used for a capillary array electrophoresis apparatus, in that a buffer liquid injection port to be installed at a buffer liquid container, a light detection portion where laser beam is irradiated and fluorescence is detected and a specimen introduction portion into which a sample is introduced and to which a voltage necessary for causing electrophoresis is applied, are used.

As illustrated in FIG. 8, the capillary array electrophoresis apparatus is constituted by a capillary array 402, an injection port 404 of buffer liquid and electrophoresis medium, a light detection portion 403 and a sample introduction portion 405. Further, an electrode is secured to capillaries at the sample introduction portion 405 of the capillary array.

By making use of a second syringe 410 in a polymer solution pump, i. e. a gel injection pump system 414 which is shown in a simplified form, electrophoresis medium and buffer liquid are injected under pressure from a buffer liquid reservoir 412 to the gel injection portion 404 in the capillary array 402. A high voltage is applied between an electrode 407 provided in the buffer liquid reservoir 412 and the electrode portion 405 of the capillary array.

Figure 13:
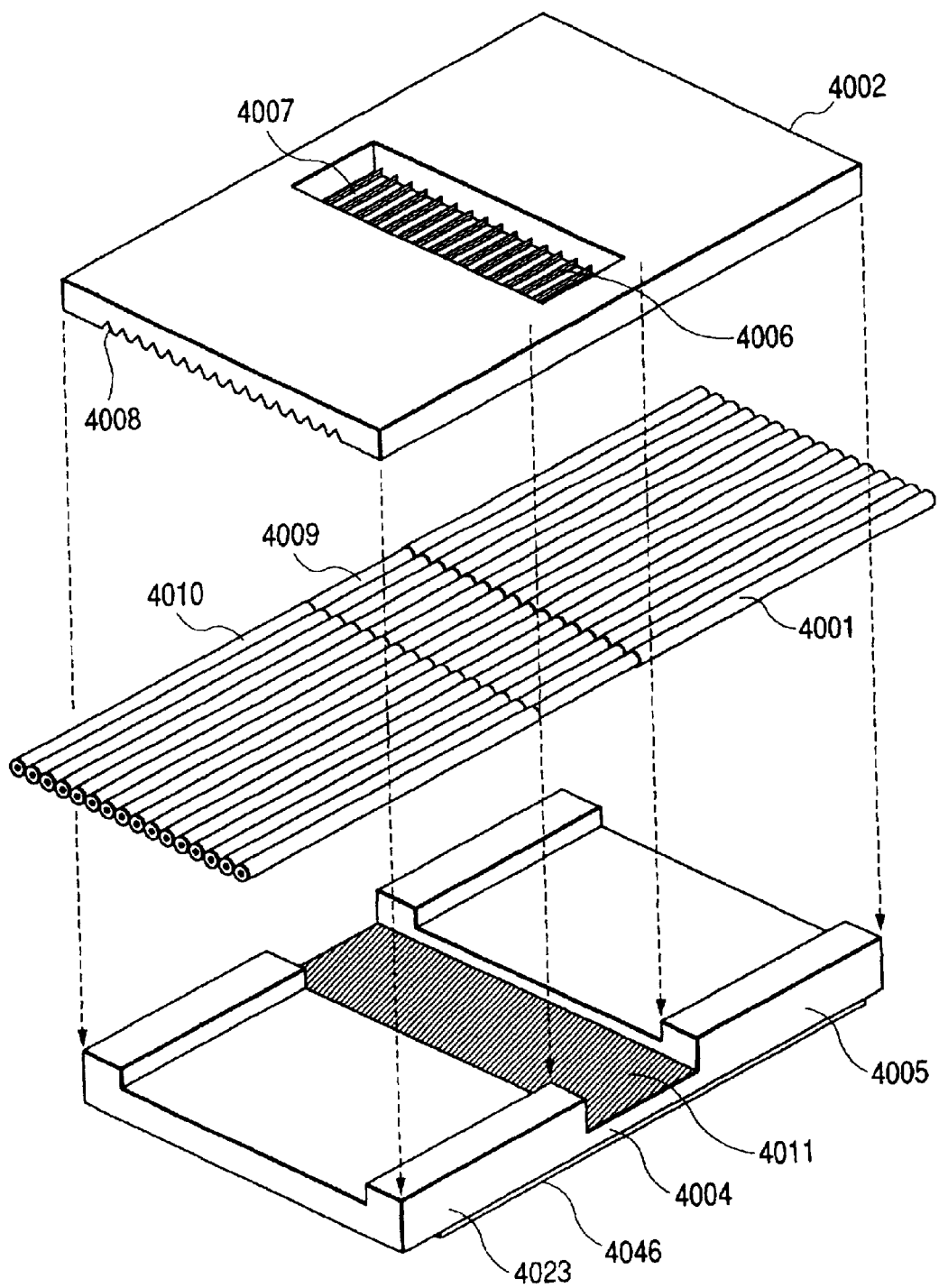
FIG. 13 is a exploded view showing a structure of an irradiation and detection portion in a capillary array used in the present invention.

An entire layout and operation of an electrophoresis apparatus using a capillary array according to the present invention will be explained with reference to FIG. 12. The capillary array according to the present invention includes a buffer liquid injection port 3010 which is formed by bundling a plurality of capillaries at one ends thereof and is set to a buffer liquid container 3117 for injecting buffer liquid 3136, and a portion where the coating of the plurality of capillaries is removed of which details are illustrated in FIG. 13.

The coating removed portion of the capillaries is arranged in a plane and held on a holder substrate 4005. The holder substrate 4005 is provided with a window 4011 for passing detection light at a portion corresponding to the coating removed portion of the respective capillaries. The holder substrate 4005 further includes a light detection portion provided with a light shielding region defining the window for passing the detection light.

In FIG. 12, at the other ends of the capillaries, a sample introduction portion 3032 is constituted into which a sample marked by a fluorescent material so as to supply the fluorescent sample into the capillary array, and near the respective capillaries at the top end of the fluorescent sample introduction portion an electrode (not shown) is provided onto which a voltage necessary for electrophoresis is applied. The voltage necessary for the electrophoresis is applied between the electrode provided at the capillary array holder 3030 and a reservoir 3117 for supplying the electrophoresis medium from a power source 3119.

As illustrated in FIG. 12, the capillary array electrophoresis apparatus is constituted by such as a sample measurement portion 3116, a buffer liquid container 3117, a fluorescent sample container 3118, a high voltage power source 3119, an optical system comprising a laser beam source 3120, a mirror 3121, a beam splitter 3122, a condenser lens 3123, a first lens 3124, an optical filter and transmission type grating 3125, a second lens 3126, and a CCD camera 3127, and a processing unit 3128. The sample measurement portion 3116 is constituted by capillaries 3001, a light detector, i. e. a light detection portion 3020, a buffer liquid injection port 3010 and a conductive fluorescent sample injection port 3032.

Now, the operation principle of the capillary array electrophoresis apparatus will be explained with reference to FIG. 12. The laser beam 3133 generated from the laser beam source 3120 is divided into two parts by the beam splitter 3122 and the advancing direction thereof is changed by the mirror 3121. The laser beam 3133 is condensed by the condenser lens 3123 and is irradiated to the capillaries 3001 from a direction in parallel with the alignment direction of the capillaries 3001. The inside of the capillaries 3001 is filled with the sample marked by a fluorescent material (fluorescent sample 3134), and when the laser beam 3133 is irradiated, the fluorescent sample 3134 emits fluorescence 3135. For the detection of the fluorescence 3135, the fluorescence 3135 emitted in substantially perpendicular direction with respect to the alignment plane of the capillaries 3001 is converted into parallel light by the first lens 3124, is effected of image/color division by the optical filter and transmission type grating 3125, and thereafter image-formed on the CCD camera 3127 by the second lens 3126 and is detected by the CCD camera 3127. The detected measurement data is processed by the processing unit 3128.

In FIG. 12, the laser beam 3133 is irradiated from the both sides of the light detection portion 3020, however, the apparatus can be constituted in such a manner that the laser beam 3133 is irradiated only from one side thereof. Further, the layout of the light receiving optical system is not limited to that illustrated in FIG. 12. Still further, the number of constituting capillaries is not limited to 16 pieces and the structure of the buffer liquid injection port 3010 and the conductive fluorescent sample injection port 3032 is not also limited to those shown in FIG. 12.

Now, an operation sequence of the capillary array electrophoresis apparatus will be explained. The buffer liquid 3136 contained in the buffer liquid container 3117 is injected into the capillaries 3001 from the buffer liquid injection port 3010. Subsequently, the conductive fluorescent sample injection port 3032 is immersed in the fluorescent sample container 3118 filled with the fluorescent sample 3134 and the fluorescent sample 3134 is injected into the capillaries 3001. Thereafter, the conductive fluorescent sample injection port 3032 is immersed in a buffer liquid container (not shown) containing buffer liquid, and a high voltage is applied between the buffer liquid injection port 3010 and the fluorescent sample injection port 3032 by the high voltage power source 3119 to thereby cause electrophoresis in the capillaries. Since the moving speed by electrophoresis is proportional to the electric charge magnitude of the molecules and is reverse proportional to the mass of the molecules, the fluorescent sample 3134 is separated. Through continuous application of the high voltage for a long time the electrophoresis is caused for a long time and the fluorescence 3135 emitted at this time is continuously measured.

The sample introduction portion 3030 is structured by inserting capillaries into stainless tubes. Respective stainless tubes 3321 are soldered to an electrode plate with a protective cover and through application of a voltage to a connecting portion 3031, the voltage is applied to all of the stainless tubes. As has been explained, since the capillary array itself is provided with all necessary functions including the buffer liquid injection port 3010 attached to the buffer liquid container 3117, a light detection portion 3020 in which laser beam is irradiated and the fluorescence is detected and the sample introduction portion 3030 through which the fluorescent sample 3134 is introduced and a voltage necessary for electrophoresis is applied thereto, when an exchange of the capillary array is required, the capillary array can be exchanged with a very easy handling.

Further, the top of the fluorescent sample injection port 3032 is sealed by an adhesive so as to prevent carry over of such as the sample. A kind of the adhesive used is an epoxy series adhesive and the same is fully cured so as not to affect the electrophoresis. Gaps between capillaries 3001 and insertion portions 3033 therefor in the sample introduction portion 3030 and between the fluorescent sample injection port 3032 and the protective covers are sealed with an adhesive. Thereby, a possible electric insulation reduction is prevented which can be caused when water contained in the sample and the buffer liquid penetrates into the covers of the stainless tubes.

When once detaching the capillary array from the apparatus and storing the same after measurement of the sample, a dry preventive container cover (not shown) is attached so as not to dry the buffer liquid 3136. The container cover is a dry preventive cover for the sample introduction portion 3030. The container cover is attached to the sample introduction portion 3030 while charging pure water therein. The container cover is provided with an O ring to thereby prevent a possible drying. It is also effective to provide a dry protective cap (shown) for the buffer liquid injection port 3010. In such instance the cap is set onto the buffer liquid injection port 3010 under the condition in which a small amount of pure water is likely filled therein. When the inner diameter of the cap is determined smaller than the outer diameter of the buffer liquid injection port 3010 by about 5~15% to thereby prevent a possible drying. As a material of the cap silicon rubber is preferable, because the silicon ribber causes no adverse effect to the buffer liquid and the electrophoresis. These cover and cap also work to protect the top end thereof and to prevent contamination thereof when shipping the capillary array to a customer.

Each of the capillaries 3001 used in the capillary array as explained above is a fused quartz tube having inner diameter of 50±10 $\mu$m and outer diameter of 340±20 $\mu$m. Since the fused quartz tube itself breaks very easily, a polyimide coating having thickness of 15±5 $\mu$m is applied on the surface of the capillary. In view of limiting the amount of fluorescent sample 3134 it is desirable to reduce the inner diameter of the capillary, however, on the other hand in view of a concave lens effect due to refractive index difference between the fluorescent sample 3134 and fused quartz, the capillary having a too small inner diameter makes the measurement difficult. Therefore, the inner diameter of 50~100 $\mu$m is preferable for the fused quartz tube. Further, in order to suppress the above refractive index difference it is preferable that the outer diameter of the fused quartz tube is small, however, a too small outer diameter makes assembling thereof difficult because of static electricity, therefore, the outer diameter of 250~350 $\mu$m is preferable for the fused quartz tube. The coating material for the capillary 3001 is not limited to the polyimide, a material having an equivalent electrical insulation and other properties as those of polyimide can be used.

FIG. 13 is an exploded view of a structure of an irradiation and detection portion in a capillary array used for the present invention. Glass substrate 4023 includes a groove 4011 for laser irradiation and a black coating 4046 on the back face of the substrate. The surface of the glass substrate 4023 where the polyimide coating contacts is processed in such a high accuracy that interference fringes can be observed on the surface, and the flatness degree thereof is high.

A plurality of a capillaries 4001 are contacted to the highly flattened surface via the polyimide coating and are aligned thereon. Thereby, the plurality of the capillaries 4001 follow the glass substrate 4023 and are aligned thereon with high accuracy and easily.

The polyimide coating of the capillaries at the irradiation and detection portion is removed to constitute a transparent portion 4009. The removal can be performed, for example, in such a manner that after removing the polyimide coating by a predetermined size one by one separately, then the removed portions are arranged. However, when the polyimide coating is removed one by one by a predetermined removing width, a processing error is caused and the removed width varies. Further, the arrangement is performed in such a manner that the removed portions, in particular, the boundaries (the boundary where the polyimide resin 4010 is cut out) align each other, however, such operation likely causes error and takes time.

Usually, a non alignment of the boundary portion can be immediately recognized. In the worst case, a remaining polyimide resin can be observed from a through window 4006 which causes great adverse effect to the detection.

Therefore, instead of the one by one coating removal, after arranging the plurality of capillaries when the polyimide coating is removed collectively, the removed portions of polyimide resin 4010 on the plurality of capillaries are neatly aligned. It is easily recognized which aligning method is used when observing the alignment of the boundaries. The predetermined width and the predetermined position of the polyimide resin removed position can be freely changed inclusively with the plurality of the capillaries.

The capillaries 4001 are sandwiched by the glass substrate 4023 for the irradiation and detection portion and an opposing member 4002. The opposing member 4002 is provided with the detection through window 4006 and fluorescence is emitted from a transparent capillaries 4007. Grooves 4008 which press capillaries inner face of the opposing member 4002.

When no black coating 4046 is provided, the laser beam penetrates and passes through the plurality of capillaries which are aligned in a high accuracy. At this moment, scattered light from the surface of the capillaries passes through the glass substrate 4023 and is irradiated to a fluorescent emitting material on the surface of the opposing member 4002 disposed opposite to the glass substrate 4023, and the fluorescence emitted thereby returns to the capillaries, further passes the through window 4006 and is directed to the first lens which causes noises. Further, when a fluorescent emitting material is deposited on the back face of the glass substrate 4023, such likely causes noises.

However, when the black coating 4046 is applied on the back face of the glass substrate 4023, even if a fluorescent emitting material is contained in the opposing member 4002 and further a fluorescent emitting material is deposited after the black coating 4046 is applied, the scattered light is absorbed by the black coating 4046, thereby, the causes of noises are removed. As a material of the black coating a paint which emits no fluorescence is used. As a typical paint application work a sick screening is used, however, other painting method can be used, and further a manual painting can also be used.

An optical system according to the present invention will be explained. In an embodiment according to the present invention, laser beam is irradiated to one or both end sides capillaries in the capillary array constituted by a plurality of capillaries arranged on one flat plane, the laser beam successively propagates the adjacent capillaries and crosses the capillary array, and a CCD camera is used as a fluorescent detection means in the capillary array electrophoresis apparatus. In this instance, the alignment portion of the capillary array constituting the irradiation and detection portion is disposed in parallel with the laser beam irradiation direction. More specifically, the irradiation and detection portion is placed vertically, and the laser beam is irradiated to the irradiation and detection portion from upper direction or from upper and lower directions after dividing the laser beam into two portions. FIG. 8 shows such arrangement. Further, for the sake of illustration, the irradiation and detection portion is disposed horizontal in FIG. 12, however, the same is actually disposed vertically as in FIG. 8 and the laser beam is irradiated onto the irradiation and detection portion of the capillary array from upper and lower directions after being divided into two portions. Such arrangement is suitable for reducing the size of the optical system for the irradiation and detection. With this arrangement in connection with the laser beam, the passage of the laser beam is constituted so as not to direct to the side where an operator usually works which enhances safety.

A light emission intensity from a single capillary is determined as one which is detected by a number of CCD pixels nearest to the full width at half maximum in an emitted light distribution curve of the capillary in the capillary alignment direction with respect to the formed image on the CCD camera. Further, the optical system further includes a rotation angle adjustment function having a rotation angle accuracy of about 0.1° around the optical axis for the CCD camera and the grating.

Figure 16:
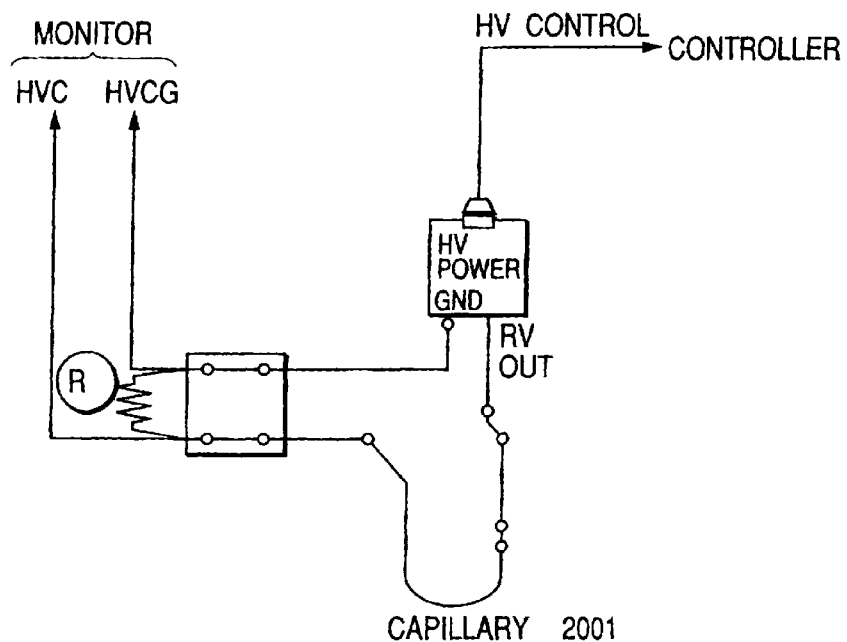
FIG. 16 is a connection diagram showing an example of methods of monitoring capillary current.

In a capillary electrophoresis DNA sequencer, when causing electrophoresis of a sample through a high voltage application onto the capillaries, whether the electrophoresis is correctly performed is judged by monitoring a current flowing through the capillary. Generally, such monitoring is performed by a built-in meter in the high voltage power source, however, when an insulation around the high voltage electrode is poor, a leakage current is caused, thereby, the meter indicates a current value including the leakage current other than the current actually flowing through the capillary which is one of drawbacks. Therefore, as illustrated in FIG. 16, a resistor R is inserted between the end of the capillary and the ground, and only the current flowing the capillary is correctly monitored through measurement of a voltage between the resistor R, thereby, whether the electrophoresis is correctly performed is correctly judged.

When effecting a capillary electrophoresis, it is necessary to apply a voltage from several kV to several 10 kV to a sample. In the present invention, in order to fulfill the above necessity a method in which a needle is inserted together with a capillary into the sample from the capillary holder is used. When an insulation between the needle and a surrounding metal portion is poor, a discharge from the high voltage portion is induced which prevents a correct measurement. In order to enhance the insulation property, it is conceived to increase the distance between the needle and the surrounding metal portion depending on the applied voltage, however, such measure is structurally limited. In the present invention, with regard to the portions which come close inherently because of structure reason, an enclosed structure with an insulation material is used. Further, a portion which applies a high voltage to the capillary holder is made detachable, and thus in order to realized the enclosed structure a plug-in structure is employed and the closedness is achieved by a rubber.

Figure 14:
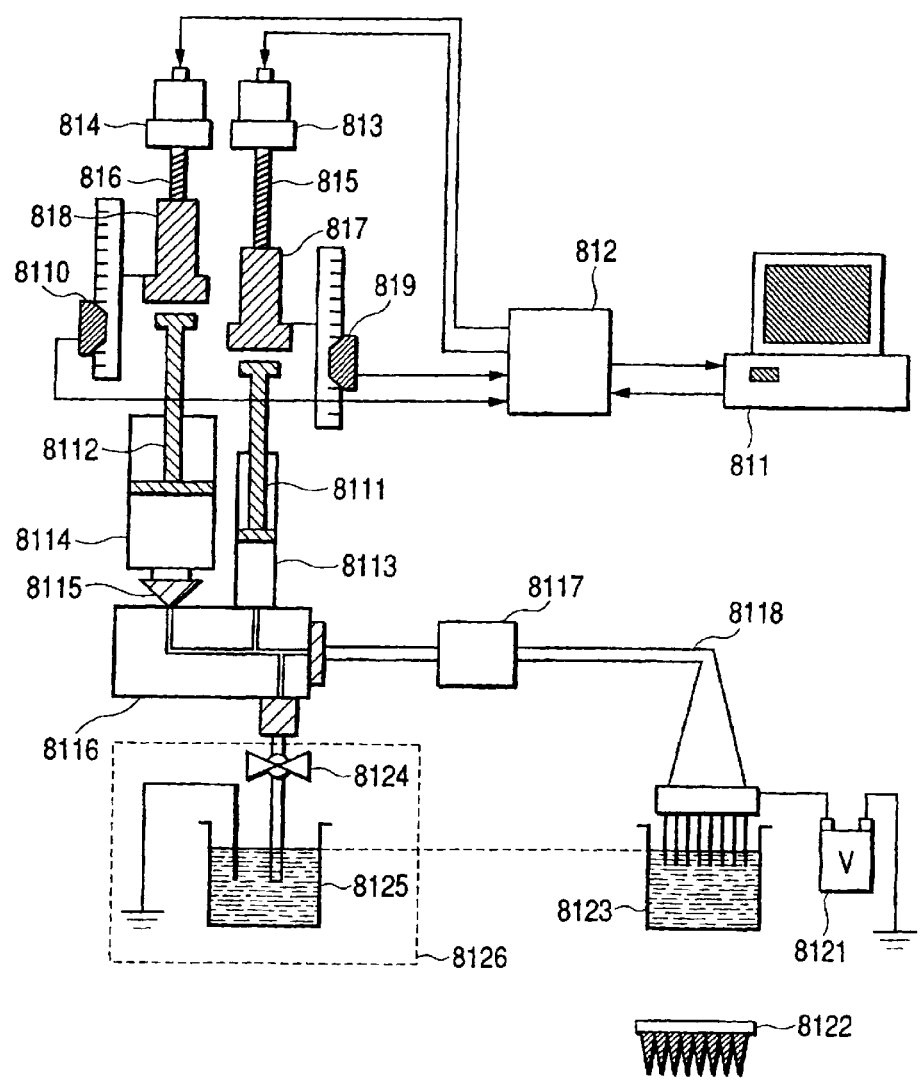
FIG. 14 is a schematic diagram for explaining a gel pump system according to the present invention.

A unit pump in an embodiment according to the present invention will be explained with reference to the drawing. FIG. 14 is a schematic diagram of an electrophoresis apparatus with a gel injection mechanism representing an embodiment according to the present invention.

A capillary array 8118 is constituted by at least two capillaries and one ends thereof are inserted into a block 8116 and the other ends thereof are integrated with an electrode which is connected to a power source 8121.

Prior to a measurement, gel serving as a separation medium or an electrophoresis medium is charged into the capillary array 8118 from the side of the block 8116. To the block 8116 an injection use syringe 8113 which injects gel into the capillary array and a refill use syringe 8114 for refilling gel into the injection use syringe 8113 are attached. The volume of the refill use syringe 8114 serving as a first syringe is larger than the volume of the injection use syringe 8113 serving as a second syringe. Further, the volume of the second syringe is basically determined as one which can supply an amount of gel polymer for one time separation and analysis. In the block 8116, a first flow passage communicating between the refill use syringe 8114 and the injection use syringe 8113 and a second flow passage communicating between the injection use syringe 8113 and the capillary array 8118 are formed. Further, the second flow passage is provided with a branch passage to a buffer reservoir 8126 which is kept at the ground potential during electrophoresis.

Further, in the flow passage communicating between the refill use syringe 8114 and the injection use syringe 8113 a check valve 8115 is inserted so as to prevent a reverse flow of gel to the refill use syringe 8114. The refill use syringe 8114 and the injection use syringe 8113 are pressed by respective drive units 817 and 818 which are controlled by a control unit 812. To the drive units 817 and 818 respective linear encoders 819 and 8110 are installed, and through reading values indicated by the linear encoders 819 and 8110 positional information of the drive units 817 and 818 is transferred to a computer 811 via the control unit 812.

After being filled with gel, the capillary array 8118 is moved to a sample container 8122, and after sucking in the sample through an electrical action, the capillary array 8118 is moved to a buffer vessel 8123. When a voltage is applied via the electrode portion for the capillary in the buffer vessel 8123, an electric field is induced in the capillaries and the introduced sample begins electrophoresis. Because of difference in electrophoresis speed depending on such as molecular weight of the introduced sample, a separated sample can be detected at a detection portion 8117. When completing an analysis, the inside the capillary array 8118 is replaced by a new gel by the injection use syringe 8113 and again the following measurement is started.

Figure 15:
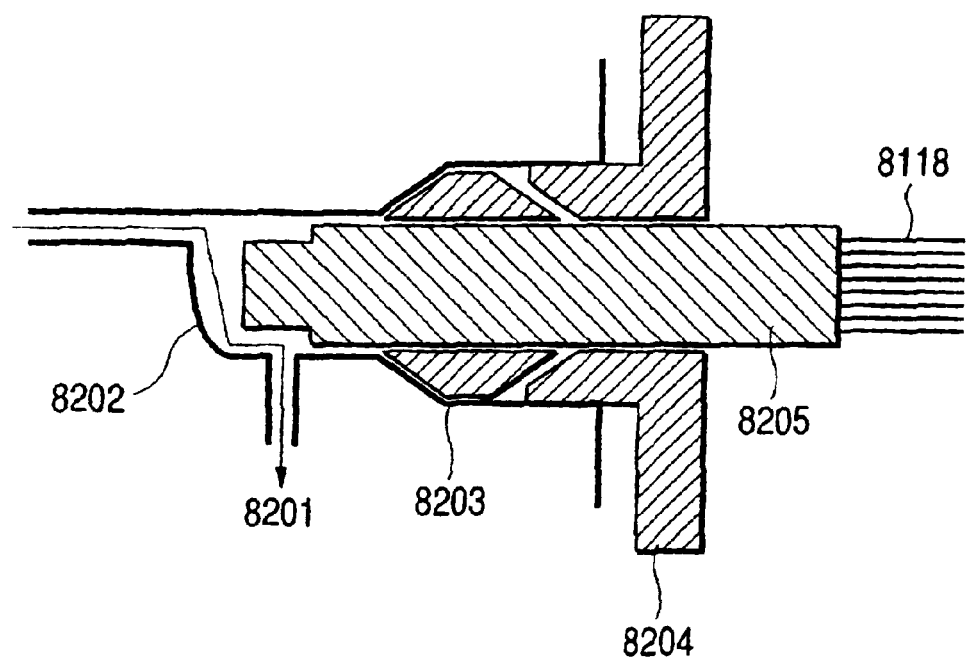
FIG. 15 is a detailed cross sectional view of a connection portion between the gel pump system and the capillary array as shown in FIG. 14.

FIG. 15 shows a cross sectional view of a connecting portion between the capillary array and the pump system. In order to prevent an invasion of bubbles into the capillaries from the connecting portion, the present structure is provided with a bubble vent structure 8201 at a flow passage 8202 in the pump system. Further, through shaping the top end of a ferrule 8205 into WD type (a long circle type), a simultaneous rotation of the ferrule 8205 when fastening a push screw 8204 is prevented. Further, through elongation of the ferrule 8205 so as to extend from the push screw, an exudation of the gel is prevented. Still further, through forming the sleeve independent, exchange thereof is enabled.

When a refillable gel is used, it is necessary that the pressures at both ends of the capillary are kept equal so as not to move the gel therein. Therefore, the liquid surfaces of the buffer vessels for both cathode and anode have to be kept at the same levels. In the present embodiment, since the block is divided into upper and lower blocks, therefore, the lower block serving as a buffer vessel is arranged to assume the same height as the other buffer vessel and the other upper block is disposed at a position where the gel is injected easily (actually at a position where the shortest capillary can reach).

Figure 18:
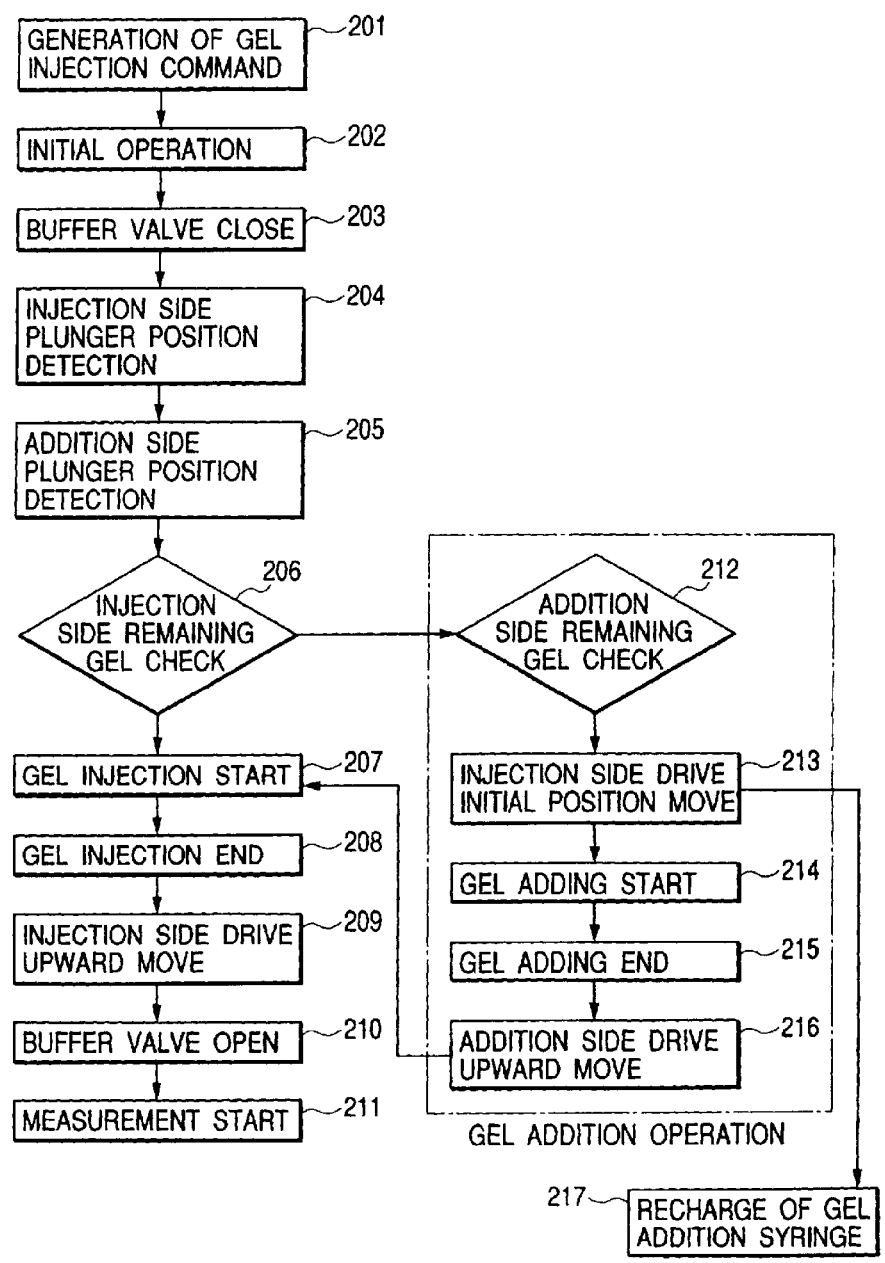
FIG. 18 is a flow chart for explaining sequence of gel injection into capillary array by the gel pump system.

FIG. 18 shows a flow chart for a gel injection work. The control unit 812 which has received a gel injection command from a computer 811 at first performs an initial operation for the gel injection unit (step 202) and closes the buffer valve 8124 (step 203). Thereafter, the drive unit 817 moves down and the position of the plunger 8111 for the injection use syringe 8113 is automatically detected (step 204). Subsequently, at the side of the refill use syringe 8114 the drive unit 818 moves down to the position of the plunger 8112 (step 205). Thereafter, based on the value of the injection side linear encoder 819 the amount of remaining gel in the injection use syringe 8113 is confirmed for the first time (step 206). When the gel in the injection use syringe 8113 is short, prior to gel injection, gel refilling operation from the refill use syringe 8114 to the injection use syringe 8113 is performed.

The gel refilling operation is performed as follows. At first, based on the value of the refill side linear encoder 8110 a gel remaining amount is confirmed (step 212). When the remaining amount is sufficient, the injection side drive unit 817 moves to a plunger position where the injection use syringe 8113 is full (step 213), thereafter a pressurization for the refill use syringe 8114 by the drive unit 818 is started (step 214). At this moment, almost all gel pushed out from the refill use syringe 8114 and flown into the block 8116 flows into the injection use syringe 8113 while lifting the plunger 8111 for the injection use syringe 8113, not into the capillaries because of difference in flow passage resistance. When the injection use syringe 8113 is filled, the plunger 8111 hits the injection side drive unit 817 to prevent further gel refilling. At this instance, the control unit 812 confirms periodically (for example, an interval of 1 sec.) the value of the encoder for the drive unit 818, and if no change is observed for 5 sec. in that if the drive unit 818 does not move, the control unit 812 judges that the gel refilling operation has been completed and stops the motor (step 215). After completing the gel refilling, the refill side drive unit 818 moves upward so as to release the pressure and waits for the subsequent command (step 216). If the remaining amount of the refill use syringe 8114 is short, a message of remaining amount shortage is displayed on the screen of the computer 811, in such instance after refilling the gel into the refill use syringe 8114 through manual operation by a user, the operation is restarted (step 217).

When the remaining gel amount in the injection use syringe 8113 is sufficient or after the gel refilling has been completed, the injection side drive unit 817 starts to press the injection use syringe 8113 and the gel injection into the capillaries 8118 is started (step 207). At this moment, the check valve 8115 prevents a gel reverse flow into the refill use syringe 8114 and further, since the buffer valve 8124 is closed, the pushed out gel from the injection use syringe 8113 flows into the capillaries which are only flowable passages. When a predetermined amount of gel is charged, the injection side drive unit 817 stops the pressurization (step 208) and moves upward so as to release the pressure and waits for the following command (step 209). Subsequently, after the buffer valve 8124 is opened (step 210), a voltage is applied to the electrode for the capillaries to start an electrophoresis (step 211).

In a DNA sequencer, the gel in the capillaries has to be refilled for every measurement, therefore, it is necessary to generate a high pressure for injecting the gel having a higher viscosity into the capillaries and to ensure a capacity of carrying out a continuous injection. However, both the cross section of a piston and the capacity of a high pressure resistant syringe are generally small. Namely, since it was difficult to obtain a syringe which satisfies the both requirements with regard to high pressure resistance and large capacity at the same time, in the present invention a combination of the injection use syringe having a high pressure resistance and the refill use syringe having a large capacity is employed. Further, in order to perform the injection and refilling automatically the structure making use of the check valve is necessitated. Further, when the gel in the refill use syringe becomes empty, the gel refilling is manually performed by a user, in this instance the syringe is detached for refilling. After attaching the syringe, the apparatus according to the present invention automatically recognizes the position of the plunger for the syringe through the plunger position detecting function, therefore, an automatic continuous measurement can be effected immediately after the user attaches the syringe to the apparatus.

Figure 19A:
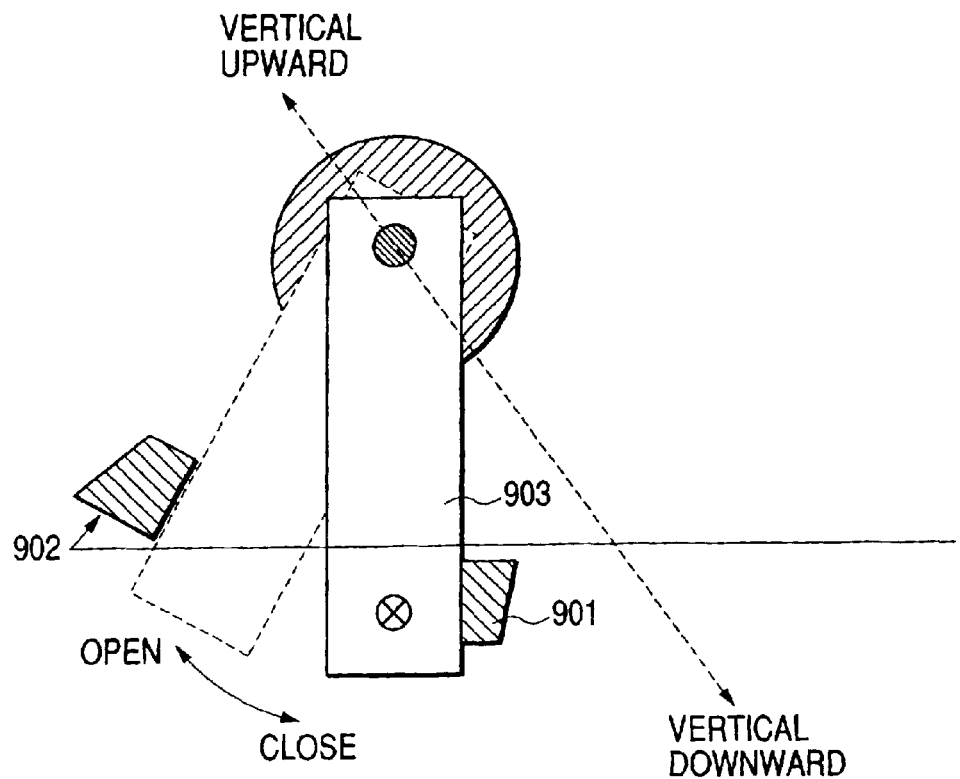
FIGS. 19A and 19B are schematic diagrams for explaining a mechanism which automatically stops generation of laser beam, when the operation of the capillary array electrophoresis apparatus according to the present invention is stopped.
Figure 19B:
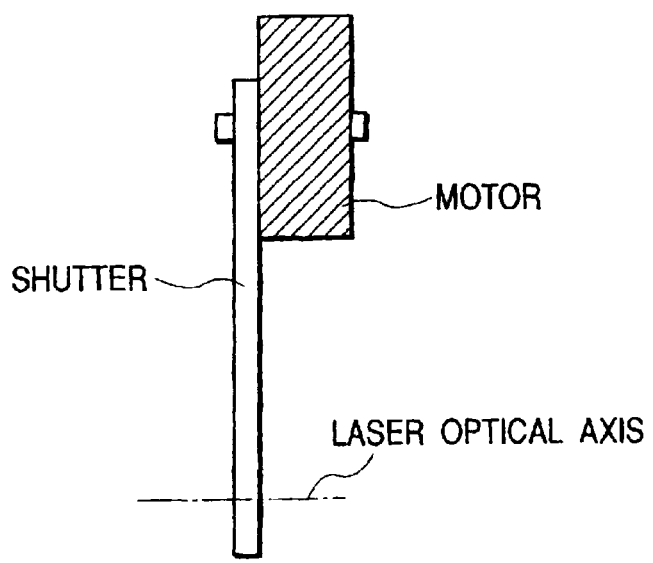

As a measure of safety operation according to the present invention, a shutter for laser beam is constituted as shown in FIGS. 19A and 19B in which a metal plate shutter 903 is attached to a reversible stepping motor, two shock absorbing rubbers 901 and 902 are disposed within a range of the shutter reciprocating movement and the shutter 903 hits to the shock absorbing rubbers at the time of open and close and stops there. Further, the attachment angle in rotational direction of the shutter to the motor is adjusted so that the shutter does not cross the vertical axis during the open and close operation thereof.

With the shutter which is constituted by attaching the metal plate to the reversible stepping motor, a vibration is caused during opening and closing of the shutter. As a result, even under a closed condition the laser beam leaks the shutter and causes a fluctuation in exposure time or abnormality when reading CCD signals. Further, depending on the attachment angle to the motor the shutter can not keep closed condition during turning off of the power source due to the weight thereof.

When a part of a plane of the glass base at the side where the capillary array is aligned is pressed to all of or a part of an array attachment reference plane in the optical system, the array attachment reference plane representing the reference plane at the side of the electrophoresis apparatus coincides with the glass base representing the reference plane at the side of the capillary array.

At the side of the electrophoresis apparatus the position of the laser beam with respect to the array attachment reference plane is determined at a positional accuracy below 10 μm. When determining the position of the laser beam with the laser beam condenser lens, the position of the laser beam condenser lens with respect to the array attachment reference plane is determined at a positional accuracy below 10 μm. In this instance, the laser beam which makes incident to the lens with a predetermined angle can be irradiated at a predetermined position on the capillary array.

At the side of the capillary array through pressing the capillaries on to the glass substrate, the position of the capillaries with respect to the glass substrate is determined at a positional accuracy below 10 μm. Accordingly, by pressing the array attachment reference plane to the glass base, the positions of the capillaries and the laser beams can be determined at a positional accuracy of about 10 μm with a good reproducibility.

According to the present invention, an electrophoresis apparatus in which capillary arrays having a variety of length can be easily exchanged and held and further can be easily adapted to a variety of modifications of separation and analysis objects.

What is claimed is:

1. A capillary array electrophoresis apparatus comprising:
   a thermostatic oven which is permitted temperature adjustment and in which space is adapted to accommodate selectively one of a plurality of capillary arrays of different length;
   a plurality of capillaries of a selected one of the plurality of capillary arrays of different length, wherein said plurality of capillaries are disposed in a predetermined position in the space of the thermostatic oven so that the plurality of the capillaries neither tangle each other nor concentrate in a bundle shape;
   an excitation light system which irradiates excitation light to the capillaries;
   a light receiving optical system which detects fluorescence; and
   a power source which applies a voltage between the ends of the capillaries.

2. A capillary array electrophoresis apparatus according to claim 1, wherein one end of the selected capillary array, into which a sample is introduced, is arranged at the bottom of the thermostatic oven and the other end thereof is projected from the side of the thermostatic oven.

3. A capillary array electrophoresis apparatus according to claim 1, wherein one end of the selected capillary array is projected from the thermostatic oven and is irradiated by the excitation light at the outside of the thermostatic oven to thereby permit the detection of fluorescence.

4. A capillary array electrophoresis apparatus according to claim 1, wherein one end of the selected capillary array is projected from the thermostatic oven and is irradiated by a laser beam at the outside of the thermostatic oven, and an array plane face constituting a detection portion of the selected capillary array to which the laser beam is irradiated is arranged to be substantially parallel to the laser beam.

5. A capillary array electrophoresis apparatus according to claim 1, further comprising a separator which holds the capillaries in the selected capillary array in a one-by-one manner.

6. A capillary array electrophoresis apparatus according to claim 1, further comprising a separator which holds the capillaries in the selected capillary array in a one-by-one manner, wherein attachment and detachment of the separator in the thermostatic oven can be performed through a separator holder.

7. A capillary array electrophoresis apparatus according to claim 1, further comprising a separator which holds the capillaries in the selected capillary array in a one-by-one manner, wherein the separator is arranged at a predetermined position in the thermostatic oven depending on the length of the selected capillary array.

8. A capillary array electrophoresis apparatus comprising:
   a thermostatic oven which is permitted temperature adjustment and in which space is adapted to accommodate selectively one of a plurality of capillary arrays of different length;
   a plurality of capillaries of a selected one of the plurality of capillary arrays of different length, wherein said plurality of capillaries are disposed in a predetermined position in the space of the thermostatic oven while being bent in one of a plurality of directions depending on the length thereof;
   an excitation light system which irradiates excitation light to the capillaries;
   a light receiving optical system which detects fluorescence; and
   a power source which applies a voltage between both ends of the capillaries.

9. A capillary array electrophoresis apparatus according to claim 8, wherein one end of the selected capillary array, into which a sample is introduced, is arranged at the bottom of the thermostatic oven and the other end thereof is projected from the side of the thermostatic oven.

10. A capillary array electrophoresis apparatus according to claim 8, wherein one end of the selected capillary array is projected from the thermostatic oven and is irradiated by the excitation light at the outside of the thermostatic oven to thereby permit the detection of fluorescence.

11. A capillary array electrophoresis apparatus according to claim 8, wherein one end of the selected capillary array is projected from the thermostatic oven and is irradiated by a laser beam at the outside of the thermostatic oven, and an array plane face constituting a detection portion of the selected capillary array to which the laser beam is irradiated is arranged to be substantially parallel to the laser beam.

12. A capillary array electrophoresis apparatus according to claim 8, further comprising a separator which holds the capillaries in the selected capillary array in a one-by-one manner.

13. A capillary array electrophoresis apparatus according to claim 8, further comprising a separator which holds the capillaries in the selected capillary array in a one-by-one manner, wherein attachment and detachment of the separator in the thermostatic oven can be performed through a separator holder.

14. A capillary array electrophoresis apparatus according to claim 8, further comprising a separator which holds the capillaries in the selected capillary array in a one-by-one manner, wherein the separator is arranged at a predetermined position in the thermostatic oven depending on the length of the selected capillary array.

15. A method of separating and analyzing a sample using capillary array electrophoresis comprising the steps of:

selecting one of a plurality of capillary arrays of different length for accommodating the same in a space of a thermostatic oven which is permitted temperature adjustment;

disposing a plurality of capillaries of the selected one of the plurality of capillary arrays in a predetermined position in the space of the thermostatic oven so that the plurality of capillaries neither tangle each other nor concentrate in a bundle shape;

irradiating excitation light to the capillaries from an excitation light system;

applying a voltage between the ends of the capillaries from a power source; and detecting fluorescence from the sample in the capillaries by a light receiving optical system.

16. A method of separating and analyzing a sample using capillary array electrophoresis according to claim 15, wherein one end of the selected capillary array, into which the sample is introduced, is arranged at the bottom of the thermostatic oven and the other end thereof is projected from the side of the thermostatic oven.

17. A method of separating analyzing a sample using capillary array electrophoresis according to claim 15, wherein one end of the selected capillary array is projected from the thermostatic oven and is irradiated by the excitation light at the outside of the thermostatic oven to thereby permit the detection of fluorescence.

18. A method of separating and analyzing a sample using capillary array electrophoresis according to claim 15, wherein one end of the selected capillary array is projected from the thermostatic oven and is irradiated by laser beam at the outside of the thermostatic oven, and an array plane face constituting a detection portion of the selected capillary array to which the laser beam is irradiated is arranged to be substantially parallel to the laser beam.

19. A method of separating and analyzing a sample using capillary array electrophoresis according to claim 15, wherein the capillaries in the selected capillary array are held by a separator in a one-by-one manner.

20. A method of separating and analyzing a sample using capillary array electrophoresis according to claim 15, wherein the capillaries in the selected capillary array are held by a separator in a one-by-one manner, and attachment and detachment of the separator in the thermostatic oven can be performed through a separator holder.

21. A method of separating and analyzing a sample using capillary array electrophoresis according to claim 15, wherein the capillaries in the selected capillary array are held by a separator in a one-by-one manner, and the separator is arranged at a predetermined position in the thermostatic oven depending on the length of the selected capillary array.

22. A method of separating and analyzing a sample using capillary array electrophoresis comprising the steps of:

selecting one of a plurality of capillary arrays of different length for accommodating the same in a space of a thermostatic oven which is permitted temperature adjustment;

disposing a plurality of capillaries of the selected one of the plurality of capillary arrays in a predetermined position in the space of the thermostatic oven while being bent in one of a plurality of directions depending on the length thereof;

irradiating excitation light to the capillaries from an excitation light system;

applying a voltage between the ends of the capillaries from a power source; and detecting fluorescence from the sample in the capillaries by a light receiving optical system.

23. A method of separating and analyzing a sample using capillary array electrophoresis according to claim 22, wherein one end of the selected capillary array, into which the sample is introduced, is arranged at the bottom of the thermostatic oven and the other end thereof is projected from the side of the thermostatic oven.

24. A method of separating and analyzing a sample using capillary array electrophoresis according to claim 22, wherein one end of the selected capillary array is projected from the thermostatic oven and is irradiated by the excitation light at the outside of the thermostatic oven to thereby permit the detection of fluorescence.

25. A method of separating and analyzing a sample using capillary array electrophoresis according to claim 22, wherein one end of the selected capillary array is projected from the thermostatic oven and is irradiated by laser beam at the outside of the thermostatic oven, and an array plane face constituting a detection portion of the selected capillary array to which the laser beam is irradiated is arranged to be substantially parallel to the laser beam.

26. A method of separating and analyzing a sample using capillary array electrophoresis according to claim 22, wherein the capillaries in the selected capillary array are held by a separator in a one-by-one manner.

27. A method of separating and analyzing a sample using capillary array electrophoresis according to claim 22, wherein the capillaries in the selected capillary array are held by a separator in a one-by-one manner, and attachment and detachment of the separator in the thermostatic oven can be performed through a separator holder.

28. A method of separating and analyzing a sample using capillary array electrophoresis according to claim 22, wherein the capillaries in the selected capillary array are held by a separator in a one-by-one manner, and the separator is arranged at a predetermined position in the thermostatic oven depending on the length of the selected capillary array.

* * * * *